US00PP13177P2

(12) United States Plant Patent
Mowrey et al.

(10) Patent No.: US PP13,177 P2
(45) Date of Patent: Nov. 5, 2002

(54) PEACH TREE NAMED 'SUPECHFIFTEEN'

(75) Inventors: Bruce D. Mowrey, La Selva Beach; David W. Cain, Bakersfield, both of CA (US)

(73) Assignee: Sun World International, Inc., Bakersfield, CA (US)

( * ) Notice: Subject to any disclaimer, the term of this patent is extended or adjusted under 35 U.S.C. 154(b) by 0 days.

(21) Appl. No.: 09/792,530

(22) Filed: Feb. 23, 2001

(65) Prior Publication Data

US 2002/0124288 P1 Sep. 5, 2002

(51) Int. Cl.[7] ..... A01H 5/00

(52) U.S. Cl. ..... Plt./197

(58) Field of Search ..... Plt./197

*Primary Examiner*—Bruce R. Campell
*Assistant Examiner*—Susan B McCormick
(74) *Attorney, Agent, or Firm*—Knobbe, Martens, Olson & Bear, LLP

(57) ABSTRACT

A new and distinct peach variety with large, firmly textured fruit, yellow flesh, and 50–70% red overcolor. The new variety ripens early in the season and has lower winter chilling requirements.

1 Drawing Sheet

LATIN NAME OF THE GENUS AND SPECIES OF THE PLANT CLAIMED

*Prunus persica.*

VARIETY DENOMINATION

'Supechfifteen'.

BACKGROUND AND SUMMARY OF THE INVENTION

This invention relates to the discovery and asexual propagation of a new variety of clingstone peach, *Prunus persica* cv. 'Supechfifteen'. The new variety was first hybridized by Bruce D. Mowrey on Apr. 25, 1994, and selected and evaluated by Bruce D Mowrey and David W. Cain near Mecca, Riverside County, Calif. The variety was originated by hybridization. The new variety cv. 'Supechfifteen' is characterized by possessing large, yellow-fleshed fruits that are blocky in shape with a less pronounced tip. The fruits are firm in texture, and a red overcolor is present on approximately 50–70% of the fruit surface.

The seed parent is the 'Flordaglo' variety (unpatented), while the pollen parent is the 'Flordaglobe' variety (unpatented). The parent varieties were first crossed in February 1992, with the date of sowing being October 1992. The first flowering was January 1994. The new 'Supechfifteen' variety was first asexually propagated by Bruce D. Mowrey in June 1994 by budding.

The new variety cv. 'Supechfifteen' ripens at approximately the same time as its pollen parent, the 'Flordaglobe' variety, but differs in several characteristics. 'Supechfifteen' has larger fruit (169 g compared with 115 g for 'Flordaglobe'). The new variety also has less overcolor than 'Flordaglobe', (50–70% compared to 60–80% with 'Flordaglobe'). The new variety 'Supechfifteen' has a lower chilling requirement than 'Flordaglobe', requiring approximately 150 hours of temperatures below 45° F. compared to 500 hours for 'Flordaglobe'. The new variety 'Supechfifteen' may be distinguished from its seed parent, 'Flordaglo' by having yellow flesh as compared to the white flesh of 'Flordaglo'.

The new variety cv. 'Supechfifteen' may be distinguished from presently available low-chilling varieties in commerce by several characteristics. 'Supechfifteen' ripens approximately three days before 'Flordaprince', and has larger-sized fruit than 'Flordaprince' (approximately 169 g per fruit compared to 110 g per fruit in the 'Flordaprince' variety). The new variety ripens approximately 13 days before the 'Tropic Beauty' variety.

The new peach variety cv. 'Supechfifteen' has been shown to maintain its distinguishing characteristics through successive asexual propagations by, for example, budding.

BRIEF DESCRIPTION OF THE FIGURE

The accompanying drawing in FIG. 1 illustrates in full color.

DETAILED BOTANICAL DESCRIPTION OF THE INVENTION

Figure 1:
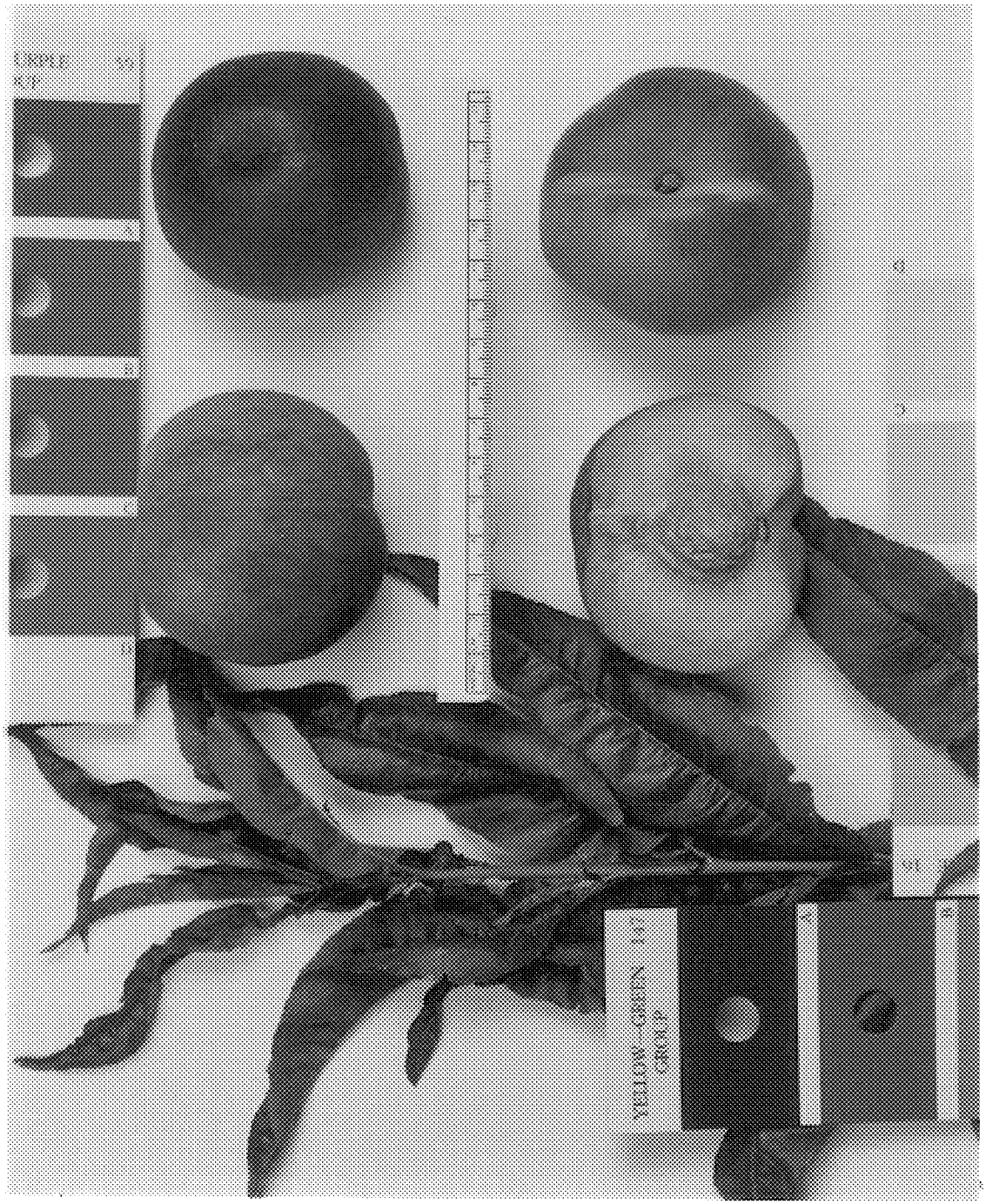

Throughout this specification, color names beginning with a small letter signify that the name of that color, as used in common speech, is aptly descriptive. Color names beginning with a capital letter designate values based upon the R.H.S. Colour Chart, published by The Royal Horticultural Society, London, England.

The descriptive matter which follows pertains to 'Supechfifteen' plants grown in the vicinity near Wasco, Kern County, Calif., during 2000, with bloom and ripe dates also given for a low chill site near Mecca, Riverside County, Calif. The descriptive matter is believed to apply to plants of the same variety grown under similar conditions of soil and climate elsewhere:

TREE

General: Trees were five years old and were maintained at a height of about ten feet and a canopy diameter of about ten feet by annual prunings.

*Size.*—Medium.
*Vigor.*—Typical of the species; shoot growth on mature tree during one growing season is about 600 mm to about 1000 mm (responding typically to irrigation, fertilization, and other cultural factors). Habit: semi-upright.
*Density of foliage.*—Medium.
*Shape.*—Vase formed.
*Hardiness.*—Hardy near Wasco in Kern County, Calif.
*Productivity.*—Productive.
*Fruit bearing.*—Regular bearer.
*Root stock.*—'Nemared'.

Trunk: Trunk is round in outline and of medium circumference, averaging 68 cm at 30 cm above ground level on 5-year-old trees.
*Shape.*—Medium.
*Surface texture.*—Smooth-medium.
*Color.*—About 199B Grey-Brown group.

Branches: Branches are round in outline and average 37 cm in circumference on 5-year-old trees as measured 30 cm distal from the branch juncture with the trunk.
*Shape.*—Medium-slender.
*Color.*—About 175C to 201D, varying with age of tree.
*Surface texture.*—Smooth-medium.
*Surface appearance.*—Semi-glossy-dull.

Lenticels:
*Number.*—Medium-few.
*Size.*—Large-medium.
*Color.*—About 161A.
*Density.*—1.6/cm$^2$.

LEAVES

General:
*Average length.*—About 18 cm.
*Average width.*—About 4.9 cm.
*Size.*—Large-medium.
*Outline.*—Lanceolate.
*Profile.*—Up folded.
*Leaf blade tip.*—Curved downwardly.
*Angle of tip.*—Acute.
*Margin.*—Finely serrate.
*Undulation of margin.*—Slight.
*Apex.*—Acuminate.
*Base.*—U-shaped.
*Thickness.*—Medium.
*Venation pattern.*—Pinnately net veined.
*Vein color.*—About 147C.

Upper surface:
*Color.*—About 147A Yellow-Green group.
*Glossiness.*—Medium.
*Pubescense.*—Absent.
*Surface texture.*—Rugose.
*Surface appearance.*—Semi-glossy.

Lower surface:
*Color.*—About 147B Yellow-Green group.
*Glossiness.*—Weak.
*Pubescense.*—Absent.
*Surface texture.*—Rugose.
*Surface appearance.*—Dull.

Petiole:
*Length.*—Medium-short, about 1 cm.
*Thickness.*—Thick-medium, about 2 mm.
*Color.*—About 147C.

Glands:
*Average number.*—5.
*Positioning.*—On both leaf base and petiole.
*Size.*—About 0.9 mm long by about 0.7 mm wide.
*Shape.*—Reniform.
*Color.*—About 153D Yellow-Green group.

Stipules:
*Persistence.*—Fall off.

Wood (leaf) buds:
*Shape.*—Ovoid.
*Size on typical 5 mm flowering shoot.*—About 1.1 mm wide at widest point by about 3 mm long.
*Position relative to shoot.*—Adpressed.
*Support.*—Decurrent.
*Time of bud burst.*—Bud burst occurs at the same time as flower bud expansion.

Flowering shoots:
*Anthocyanin coloration.*—Present.
*Intensity.*—Medium.
*Thickness.*—Thin-medium, about 0.40 cm
*Internode length.*—Medium, about 2.3 cm, midway on flowering shoots.
*Density of buds.*—Medium.
*Distribution.*—On one year old shoots.
*Ratio of wood (leaf) buds to flowering shoots.*—1:2.5.

FLOWERS

Flower-buds:
*Hardiness.*—Hardy under California conditions.
*Size on typical flowering shoot about 5 mm in diameter.*—About 4 mm long by about 3 mm in diameter at widest point.
*Length.*—Medium.
*Shape.*—Pointed — plump.
*Positioning.*—Free.
*Pubescence.*—Pubescent.
*Color.*—About 165A Greyed-Orange group.

General:
*Date of first bloom at low chill site.*—Jan. 24, 2000, near Mecca, Riverside County, Calif.
*Date of full bloom at low chill site.*—Jan. 29, 2000, near Mecca, Riverside County, Calif.
*Date of first bloom at medium-high chill site.*—Feb. 1, 2000, near Wasco, Kern County, Calif.
*Date of full bloom at medium-high chill site.*—Feb. 6, 2000, near Wasco, Kern County, Calif.
*Time of bloom.*—Medium, as compared with similar varieties in the growing area of Mecca, Riverside County, Calif.
*Duration of bloom.*—Medium, about 10 days.
*Size (diameter of the fully open flower).*—Large, about 4.8 cm.
*Shape.*—Rosaceous.
*Petals.*—Overlapping.
*Color: (fully opened flower).*—About 62D.
*Pollination requirements.*—Self-fertile.

Peduncle:
*Length.*—About 4 mm.
*Diameter.*—About 3 mm.
*Pubescence.*—Absent.

Receptacle:
*Depth.*—Medium.
*Pubescence of inner surface (at white bud stage).*—Absent.
*Pubescence of outer surface.*—Absent.

Sepals:
*Number of sepals per flower.*—5.
*Width at first opening of flower.*—About 6 mm.
*Positioning.*—Adpressed to petals.

*Shape.*—Ovate.
*Color.*—About 145A, becoming about 46A as the flower ages.
*Pubescence of inner surface.*—Absent.
*Pubescence of outer surface.*—Medium.
*Frequency of flowers with double sepals.*—None.

Petals:
*Number of petals per typical flower.*—5.
*Frequency of flowers with double petals.*—None.
*Size.*—Medium, about 1.6 cm width.
*Shape.*—Elliptical.
*Shape of apex.*—Rounded.
*Claw length.*—Medium.
*Margin waviness.*—Medium.
*Base angle.*—Medium.
*Shape of base.*—Petal narrows at point of attachment.
*Margin.*—Entire (smooth).
*Texture.*—Smooth and delicate.
*Pubescence of inner surface.*—Absent.
*Pubescence of outer surface.*—Absent.
*Color* (*inner surface*).—About 62D.
*Color* (*outer surface*).—About 62D.

Stigma:
*Position* (*as compared with anthers*).—Level.

Anthers:
*Color* (*just before dehiscence*).—About Red 46D.

Pollen:
*Color.*—About 14B.

Stamens:
*Position.*—Perigynous.

Pistil:
*Frequency of supplementary pistils.*—Few.
*Number.*—Usually one, varies from 1–2.
*Length when flower bud first opens.*—About 21 mm.

Ovary:
*Color.*—About 150D.
*Pubescence.*—Pubescent.
*Density of hairs.*—Medium.

Style:
*Pubescence* (*of base*).—Medium.
*Density of hairs.*—Slight.

FRUIT

General:
*Maturity when described.*—Firm-ripe.
*Date.*—Apr. 12, 2000 at the low-chill site near Mecca, Riverside County, Calif. May 6, 2000 at the medium-high chill site near Wasco, Kern, County, Calif.
*Size.*—Slightly variable; large, about 7.3 cm, about 169 g.
*Axial diameter.*—About 6.8 cm.
*Transverse in suture plane.*—About 7.3 cm.
*At right angles to suture plane.*—About 7.3 cm.
*Form.*—Slightly variable; globose.
*Position of maximum diameter.*—Towards middle.
*Symmetry about the suture.*—Slightly asymmetric.
*Season ripening.*—Early.
*Use.*—Fresh market.
*Keeping quality.*—Good. Fruit held firm in cold storage for 2 weeks at 38° F.–42° F. without internal breakdown of flesh or appreciable loss of eating quality.
*Resistance to.*—Insects: good. Diseases: good.
*Shipping quality.*—Good. Fruit showed minimal scarring or bruising of skin or flesh during packing or shipping trials.

Suture: An inconspicuous line; has slight-marked depression beyond pistil point.

Ventral surface:
*Shape.*—Rounded slightly.
*Lips.*—Equal.
*Depression of apex.*—Distinct.
*Pistil base.*—Not persisting.
*Pubescence at apex.*—Moderate to scant; hairs short. Density of apex pubescence: medium.

Stem cavity:
*Shape.*—Flaring; circular; with suture showing on one side.
*Depth.*—About 1.8 cm.
*Breadth.*—About 3.0 cm.

Base:
*Shape.*—Rounded.

Apex:
*Shape.*—Slightly depressed.

Pistil point:
*Shape.*—Slightly depressed.

Stem:
*Length.*—About 0.8 cm.
*Diameter.*—About 3.2 mm.
*Color.*—About 148B.
*Appearance.*—Stout, glabrous.
*Adherence to stone.*—Strong.

Skin:
*Thickness.*—Medium.
*Texture when harvested.*—Smooth and crisp.
*Reticulation.*—Absent.
*Roughness.*—Absent.
*Tenacity.*—Tenacious to flesh.
*Tendency to crack.*—None in wet season.
*Ground color.*—About 1C.
*Overcolor.*—About 59A.
*Down* (*pubescence*).—Moderate to scant.

Flesh:
*Color.*—About Green-Yellow group 1B near stem end; about Red-Purple group 59B in flesh near apex.
*Amygdalin.*—Wanting.
*Juice.*—Moderate.
*Sugar content.*—Low to medium.
*Texture.*—Medium, coarse, melting.
*Fibres.*—Abundant, coarse, tender.
*Ripens.*—Earliest at apex.
*Flavor.*—Delicate.
*Eating quality.*—Good for early season fruit.
*Stone/flesh ratio.*—1 cm diameter: 3 cm diameter.

STONE

General:
*Adherence to flesh.*—Cling — adheres to flesh over entire surface.
*Fibres.*—Long.
*Size.*—Medium.
*Length.*—About 3.2 cm.
*Width along suture plane.*—2.2 cm.
*Width at right angle to suture plane.*—1.8 cm.
*Width of stalk end.*—About 0.4 cm.
*Angle of stalk end.*—Obtuse.
*Thickness.*—About 1.2 cm.
*Form* (*profile*).—Oval.
*Form* (*ventral view*).—Globular.
*Base.*—Oblique.
*Hilum.*—Oval.

*Apex.*—Pointed.

*Position of maximum breadth.*—Middle.

*Sides.*—Equal.

*Surface.*—Regularly furrowed near base, pitted throughout.

*Outgrowing keel.*—Partly developed.

*Ridges.*—Rounded towards base.

*Pits.*—Elongated.

*Ventrical edge.*—Thin with slight wing toward base.

*Dorsal edge.*—Narrow.

*Color of stone.*—About 165D Greyed-Orange group.

*Tendency to split.*—Slight in wet season.

*Kernel size* (*when dried*).—About 10 mm wide by about 13 mm long.

*Kernel viability.*—Embryo is immature when harvested.

*Kernel color when dried.*—About yellow orange 18C.

*Kernel astringency.*—Very bitter.

*Kernel shape.*—Oval.

*Amygdalin.*—Undetected.

Supechfifteen: Table of R.H.S. Color Codes:

| | | | R.H.S. Color Code |
|---|---|---|---|
| TREE: | Trunk: | | 199B |
| LEAVES: | Upper Surface: | | 147A |
| | Lower Surface: | | 147B |
| | Glands: | | 153D |
| FLOWERS: | Flower-Buds: | | 165A |
| | General: | Fully opened flower: | 62D |
| | | Inner surface: | 62D |
| | | Outer surface: | 62D |
| | Anthers: | Just before dehiscence: | 46D |
| | Pollen: | | 14B |
| FRUIT: | Skin: | Ground color: | 1C |
| | | Overcolor: | 59A |
| | Flesh: | Near stem end: | 1B |
| | | Flesh near apex: | 59B |
| STONE: | General: | Stone: | 165D |

What is claimed is:

1. A new and distinct peach tree as herein described and illustrated.

* * * * *